United States Patent [19]
Dolisi

[11] Patent Number: 6,113,580
[45] Date of Patent: Sep. 5, 2000

[54] CERVICAL BARRIER SHIELD FOR FEMALE VAGINAL DOUCHE

[75] Inventor: Frank Dolisi, Old Brookville, N.Y.

[73] Assignee: American Maternity Products, Inc., Old Brookville, N.Y.

[21] Appl. No.: 09/141,846

[22] Filed: Aug. 27, 1998

[51] Int. Cl.[7] .......................... A61M 25/00; A61M 5/00; A61M 29/00
[52] U.S. Cl. .......................... 604/268; 604/41; 604/181; 604/187; 604/257; 606/193; 128/918
[58] Field of Search .................... 604/27, 39, 41, 604/93, 96, 181, 187, 257, 263, 212, 268, 275–276, 278, 279, 523, 524, 531, 514–15; 128/918; 222/526–27, 567; 606/193

[56] References Cited

U.S. PATENT DOCUMENTS

| | | | |
|---|---|---|---|
| 315,860 | 4/1885 | Van Buskirk | 604/275 |
| 3,817,248 | 6/1974 | Buckles et al. | 128/260 |
| 4,256,107 | 3/1981 | White | 604/248 |
| 4,775,362 | 10/1988 | Kronner | 604/96 |
| 5,104,377 | 4/1992 | Levine | 604/101 |
| 5,209,754 | 5/1993 | Ahluwalia | 606/119 |
| 5,364,375 | 11/1994 | Swor | 604/278 |
| 5,624,399 | 4/1997 | Ackerman | 604/96 |
| 5,643,311 | 7/1997 | Smith et al. | 604/96 |
| 5,645,083 | 7/1997 | Essig et al. | 604/27 |

Primary Examiner—Ronald K. Stright, Jr.
Assistant Examiner—Patricia Bianco
Attorney, Agent, or Firm—Alfred M. Walker

[57] ABSTRACT

The female vaginal douche with cervical shield is a unique device with a wide range of health implications. The device is unique because there is no existing device available that offers the ability to cleanse the vaginal mucosa without allowing a forceful flow of fluid, debris, and bacteria (both commensal and pathogenic), into the uterine cervix. At present, when vaginal douching takes place, there is no barrier in place to protect or shield the cervix from this potentially harmful practice. By combining the vaginal douche applicator with an attached cervical shield, access to the uterine cervix will be limited. The limitation theoretically prevents microorganisms from entering the upper female genital tract. Shielding the cervix during vaginal douching has the potential to prevent serious pelvic infections including pelvic inflammatory disease, tuboovarian abscess, endometritis, as well as female factor infertility and potentially life threatening ectopic pregnancy. It is also possible that other unwanted effects such as uncomfortable uterine cramps may be prevented as well. The female vaginal douche with a cervical barrier shield is applied as one unit, and can be either disposable or non-disposable. Once applied, the douche may be utilized in the typical fashion, but with possibly less complicated and unwanted side effects.

13 Claims, 2 Drawing Sheets

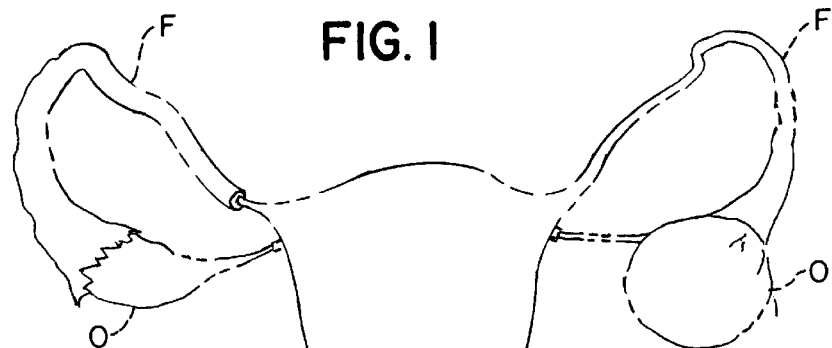
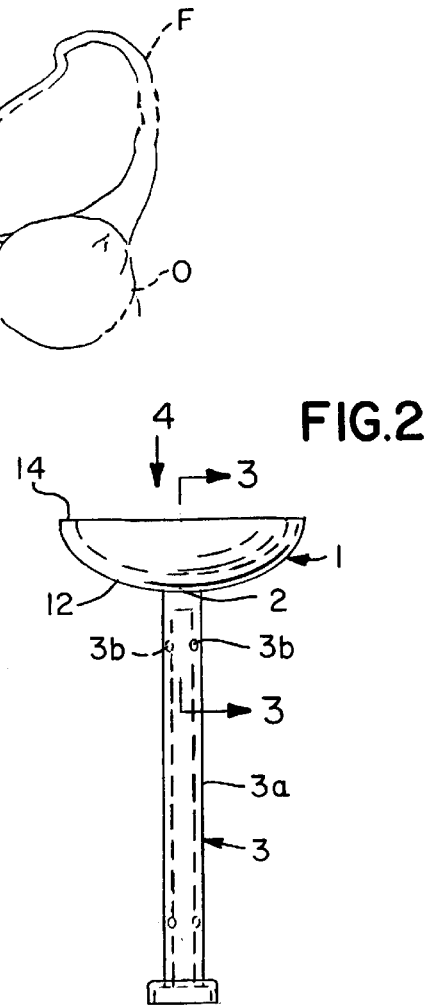
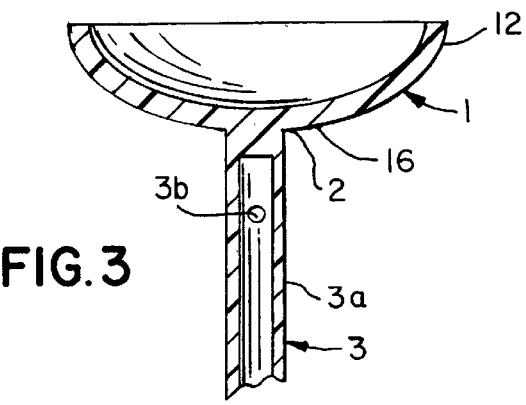
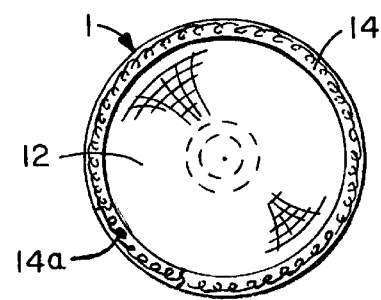

CERVICAL BARRIER SHIELD FOR FEMALE VAGINAL DOUCHE

FIELD OF THE INVENTION

The present invention relates to protective barriers for internal hygiene.

BACKGROUND OF THE INVENTION

Existing vaginal douches include hollow fluid flow applicators for dispensing fluid into a vagina. However, because of the proximity of the vagina to the cervix, leading to the uterus, there is the risk of trans-cervical contamination of the uterus with bacteria, contaminated fluid and/or debris. Serious health risks include infection, sterility, ectopic pregnancies and/or pelvic inflammatory disease.

OBJECTS OF THE INVENTION

It is therefore an object of the present invention to provide a uterine cervical shield to a vaginal douche applicator.

It is also an object of the present invention to minimize the flow of fluid, bacteria and/or debris into a cervical canal and uterus.

It is also an object of the present invention to provide a barrier which is easily insertable but which adapts to the cervix.

It is also an object of the present invention to improve over the disadvantages of the prior art.

SUMMARY OF THE INVENTION

The invention is an adaptation of the female vaginal douching systems that are available commercially at the present time. The present invention includes a uterine cervical shield that is placed at the upper, distal tip of a douche applicator. The shield covers the female uterine cervix, thereby minimizing the flow of fluid, bacteria and/or debris into the cervical canal during the process of vaginal douching.

The cervical barrier shield for a female vaginal douche, is used with a bottle for fluid preparation, and the cervical barrier shield includes a modification to a standard hollow douche applicator with one or more lateral fluid flow discharge ports. The shield includes a flexible, fluid-impervious member attached at a distal end thereof. The flexible member is foldable for trans-vaginal insertion and is subsequently expandable when opened adjacent to a female cervix. It expands and covers the cervix in a sealed relationship to prevent the flow of fluid from the douche applicator and the vagina to the cervix.

The flexible fluid impervious member includes a concave cervix engaging outer surface, with an annular rim, which is flexible and elastic to keep the cervical barrier shield open in the vaginal canal, as opposed to closing due to the pressure of the vaginal walls surrounding the cervical barrier shield.

Accordingly, several objects and advantages of the present invention are the ability to shield the female uterine cervix during the process of vaginal douching. The cervical shield thus prevents the forceful flow of the fluid used in the douche preparation from readily penetrating the uterine cervix. This may also stop the flow of debris and microorganisms, both commensal and pathogenic, commonly found in the female vagina, from entering into the uterine cavity and eventually traveling into the fallopian tubes and peritoneal cavity. The flow of vaginal fluid is thus be directed inferiorly toward the vaginal introitus and away from the cervix, yet the vaginal fornices will be reached by the douche preparation in order to allow maximal contact with the vaginal mucosa. By preventing the flow of fluid to the cervical canal there is a the possibility of reduction of serious infection, infertility, and life threatening ectopic pregnancies in women who douche.

Still further objects and advantages will become apparent from a consideration of the ensuing description and accompanying drawings.

DESCRIPTION OF THE DRAWINGS

The present invention can best be understood in conjunction with the accompanying drawings, in which:

FIG. 1 is a side elevational view of the vaginal douche applicator with a barrier shield as in the present invention, shown in use against a female cervix;

FIG. 2 is a side elevational view of the barrier shield portion of the present invention;

FIG. 3 is a close up side elevational view of the barrier shield thereof; and,

FIG. 4 is a top plan view of another embodiment thereof; shown in partial cut away to reveal an annular rim spring therein.

DETAILED DESCRIPTION OF THE PREFERRED EMBODIMENT

Figure 5:
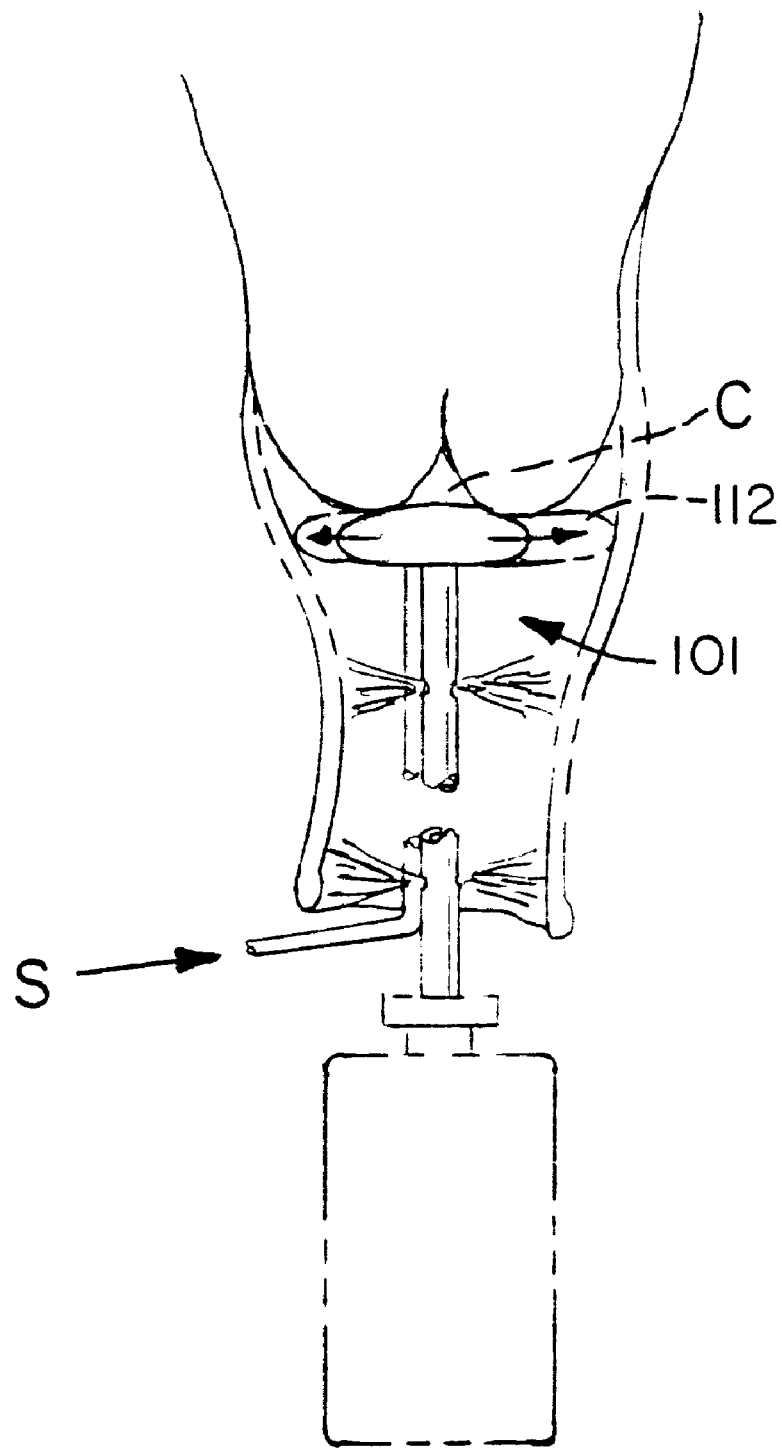
FIG. 5 is a front elevation view of another embodiment for an inflatable cervical barrier.

As shown in FIGS. 1–4, the present invention includes cervical barrier shield 1 adapted to top distal end 2 of hollow vaginal douche applicator 3. Typical vaginal douche applicator 3 is filled from a bottle 4 engagable with vaginal douche applicator 3, including hollow tube 3a having one or more transverse side ports 3b for dispensing of fluid from vaginal douche applicator 3 to vagina V.

Cervical barrier shield 1 prevents fluid flow to and through cervix C and uterus U. Cervical barrier shield 1 includes latex or plastic hemisphere 12 with flexible circular annular rim 14. Circular annular rim 14 is flexible and elastic to keep cervical barrier shield 1 open in the vaginal canal, as opposed to closed, due to the pressure of the vaginal walls surrounding cervical barrier shield 1.

Although other dimensions may be applicable preferably cervical barrier shield 1 is approximately 3–4 centimeters in diameter depending upon the size of the female cervix. Lower external convex surface 16 thereof is fixed in place to distal tip end 2 of douche applicator 3 by bonding, integral molding or medically acceptable adhesives.

Typically, douche applicator 3 is a plastic elongated device that is hollow at its center with one or more, such as four, lateral ports 3b, which ports 3b allow the flow of fluid from douche applicator 3 during the process of vaginal douching.

While other dimensions may apply, preferably the length of vaginal douche applicator 3 is approximately 8 centimeters. In shape, cervical barrier shield 1 is preferably hemispheric, with an outer concave surface 12 engagable with cervix C.

To insure that annular rim 14 of cervical barrier shield 1 is foldable upon insertion in vagina V, but expandable in place at cervix C, annular rim 14 may be made of a resilient elastomeric material, such as rubber or a synthetic plastic. Optionally as shown in FIG. 4, hemispheric cervical barrier shield 1 includes a collapsible, flexible annular edge spring 14a therein, such as a continuous foil spring, so that is foldable during insertion and expandable in use at cervix C.

USE AND OPERATION OF THE PRESENT INVENTION

The function of cervical barrier shield 1 of douche applicator 3 is to remain placed immobile inside of vagina V during the process of vaginal douching. Flexible, fluid impervious cervical barrier shield 1 mechanically obstructs uterine cervix C in such a way that fluid, microorganisms, and debris commonly found in the vagina are diverted away from cervix C, and therefore also from uterus U and other internal organs. The fluid from bottle 4 is forced inferiorly and out of vagina V, thereby reducing serious sequelae that is commonly reported in a percentage of women who practice vaginal douching.

The position of cervical barrier shield 1 at distal top 2 of douche applicator 3 allows cervical barrier shield 1 to come into contact with cervix C and subsequently direct the flow of the douching preparation to enter only vagina V, and to come into contact only with the vaginal tissue.

CONCLUSIONS, RAMIFICATIONS, AND SCOPE

Accordingly, it can be seen that cervical barrier shield 1 of the present invention shields female uterine cervix C during the process of vaginal douching. By shielding cervix C, cervical barrier shield 1 is designed to prevent and reduce the flow of microorganisms such as bacteria and parasites into uterus U, fallopian tubes F, ovaries O and peritoneal cavity. This in turn prevents serious potential problems, such as pelvic inflammatory disease, endometritis, and ectopic pregnancy in the large female population who practice vaginal douching. Cervical barrier shield 1 attached to douche applicator 3 thus limits the access of unwanted fluid with its possible contaminants from reaching organs other than the intended vaginal mucosa. The fluid thus flows out of vagina V, instead of being forced into cervix C, uterus U and beyond.

Although the description above contains many specificities, these should not be construed as limiting the scope of the invention but as merely providing illustrations of some of the presently preferred embodiments of this invention. Various other embodiments and ramifications are possible within it's scope.

For example, besides a latex or plastic shield, one may use other types of cervical blocking devices that can be conceived. One other example shown in FIG. 5 may be a shield 101 utilizing an inflatable device 112 with exterior sources of S either air of liquid. Once inserted, this device 112 may be inflated, then vaginal douching commences, with cervix C successfully shielded.

Therefore, the scope of the invention should be determined by the appended claims and their legal equivalents, rather than by the examples given.

I claim:

1. A cervical barrier shield in combination with a female vaginal douche, comprising said douche including a bottle for fluid preparation, said bottle having attached thereto a hollow applicator with lateral fluid flow discharge ports, said shield having a closed flexible fluid impervious member attached at a distal end thereof, said flexible member being foldable for trans-vaginal insertion and subsequently expandable when adjacent to a female cervix, said expanded closed flexible fluid impervious member covering the entire cervix in a sealed relationship to prevent the flow of fluid from said applicator to the cervix, said expanded, closed fluid impervious member directing fluid from the bottle away from the cervix and toward the vaginal wall.

2. The cervical barrier shield as in claim 1 wherein said flexible fluid impervious member includes a concave cervix engaging outer surface.

3. The cervical barrier shield as in claim 2 further comprising an annular rim being flexible and elastic to keep said cervical barrier shield open in the vaginal canal, as opposed to closing due to the pressure of the vaginal walls surrounding the cervical barrier shield.

4. The cervical barrier shield as in claim 3 wherein said annular rim is made of a resilient, elastomeric material.

5. The cervical barrier shield as in claim 4 wherein said annular rim is rubber.

6. The circular barrier shield as in claim 4 wherein said annular rim is a synthetic plastic.

7. The cervical barrier shield as in claim 3 wherein said annular rim includes an annular spring therein.

8. The cervical barrier shield as in claim 7 wherein said annular spring is a continuous coil spring.

9. The cervical barrier shield as in claim 1 wherein a lower external surface is fixed in place at a distal tip of the vaginal douche applicator.

10. The cervical barrier shield as in claim 9 wherein said cervical barrier shield is bonded to said douche applicator.

11. The cervical barrier shield as in claim 9 wherein said cervical barrier shield is molded integrally to said douche applicator.

12. The cervical barrier shield as in claim 9 wherein said cervical barrier shield is attached to said douche applicator by a medically acceptable adhesive.

13. The cervical barrier shield as in claim 1 wherein said cervical barrier shield is an inflatable member engagable against the cervix of a user upon inflation.

* * * * *